United States Patent

Ogura et al.

[11] Patent Number: 5,126,330
[45] Date of Patent: Jun. 30, 1992

[54] SIALOSYL CHOLESTEROL AND NEUROPATHY REMEDY COMPRISING THE SAME

[75] Inventors: Haruo Ogura, Matsudo; Kimio Furuhata, Tokyo; Shingo Sato, Iruma; Masayoshi Ito, Kunitachi; Yoshiyasu Shitori; Yoshitaka Nagai, both of Tokyo, all of Japan

[73] Assignee: Mect Corporation, Tokyo, Japan

[21] Appl. No.: 649,531

[22] Filed: Feb. 1, 1991

Related U.S. Application Data

[62] Division of Ser. No. 150,647, Jan. 7, 1988, Pat. No. 5,023,239.

[30] Foreign Application Priority Data

May 12, 1986 [JP] Japan ................................. 61-108228
Sep. 4, 1986 [JP] Japan ................................. 61-208380

[51] Int. Cl.[5] .................... A61K 31/705; C07H 15/24; C07H 5/06
[52] U.S. Cl. .......................................... 514/26; 536/5; 536/17.9; 536/18.7; 536/53; 536/55.3
[58] Field of Search .................... 514/26; 536/5, 17.9, 536/18.7, 55.3, 53

[56] References Cited

U.S. PATENT DOCUMENTS

| | | | |
|---|---|---|---|
| 4,461,762 | 7/1984 | Malinow | 514/26 |
| 4,691,012 | 9/1987 | Ogura et al. | 536/23 |
| 4,707,469 | 11/1987 | Della Valle et al. | 514/26 |
| 4,797,477 | 1/1989 | Yoshimura et al. | 536/55.3 |
| 5,023,239 | 6/1991 | Ogura et al. | 514/26 |

FOREIGN PATENT DOCUMENTS

| | | | |
|---|---|---|---|
| 0012083 | 6/1980 | European Pat. Off. | 536/5 |
| 57-35598 | 2/1982 | Japan | 536/5 |
| 62-209094 | 9/1987 | Japan | 536/5 |

OTHER PUBLICATIONS

Kogura et al.; "Summary of Proceedings of the 105th Annual Seminar of the Japanese Academy of Medicine" p. 633, Abstract 5Q9-8 (Mar. 1985).
Okamoto et al.; Chemistry Letters 9:1449-1452 (1986).
*The Merck Manual,* 15th Edition Berkow et al. Eds. pp. 1443-1448 (1987).
Kata et al.; Brain Research 438:277-285 (1988).
Ito et al.; Brain Research 481:335-343 (1989)

*Primary Examiner*—Johnnie R. Brown
*Assistant Examiner*—Nancy S. Carson
*Attorney, Agent, or Firm*—Oblon, Spivak, McClelland, Maier & Neustadt

[57] ABSTRACT

The present invention relates to a sodium salt of sialosyl cholesterol. The present compound has an excellent high water solubility, and therefore the compound is very useful as a medicine to be used for treating various diseases derived from lesions of peripheral or central nerves.

2 Claims, No Drawings

SIALOSYL CHOLESTEROL AND NEUROPATHY REMEDY COMPRISING THE SAME

This is a division of application Ser. No. 07/150,647, filed on Jan. 7, 1988, now U.S. Pat. No. 5,023,239.

BACKGROUND OF THE INVENTION

1. Field of Use

The present invention relates to sialosyl cholesterol, in particular sialosyl cholesterol which is useful as an agent for treating various diseases derived from lesions of peripheral nerves and central nerves.

2. Description of the Background

So far, it has been known in the art that sialic acid is present in many animal bodies and on the cell surface of several bacteria as a sialylated molecular complex, for example, glycoprotein, glycolipid, oligosaccharide or polysaccharide.

Recently, this compound has been thought to be important medicinally and pharmaceutically for nerve function, cancer, inflamation, immunity, viral infection, differentiation, hormone receptor, and others. Further, much attention has been paid to this compound as a peculiar active substance located on the cell surface. However, the role of sialic acid in the sialylated molecular complex has not yet been ascertained.

Furthermore, this compound has been studied by many natural organic chemists and many kinds of derivatives thereof have been obtained. However, no derivatives having a remarkable physiological activity have been obtained yet.

Further, the average span of human life has been indeed extended by various improvements in medical treatment of malignant tumor of hematopoietic organ, many kinds of cancers, and collagen disease. However, these improvements have inevitably increased use of medicines such as adrenal cortical hormone, immunosuppressant, etc. Therefore, a number of undersirable side effects such as decrease in immunological competence have arisen.

SUMMARY OF THE INVENTION

The present inventors have paid special attention to sialic acid which is a bio-inherent component and have made intensive studies on immuno-controlling agents which have substantially no side effects and exhibit a controlling activity for immunological surveillance and are obtained by chemically modifying sialic acid. As a result, the present inventors have prepared sialosyl cholesterol which is useful as a neuropathy remedy. This is based on the finding that the present sialosyl cholesterol promotes growth of the neurites of neuroblastoma cells derived from mouse (Neuro 2a), when the activity of the sialosyl cholesterol is examined by adding it to the culture of Neuro 2a.

The object of the present invention is to provide a new sialosyl cholesterol.

Another object of the present invention is to provide a new process for producing sialosyl cholesterol.

Another object of the present invention is to a new neuropathy remedy.

Incidentally, since the present sialosyl cholesterol is present in an Na salt form, the cholesterol has an excellent water-solubility and makes the utility of the cholesterol wider.

DETAILED DESCRIPTION OF THE PREFERRED EMBODIMENTS

The present invention relates to the compound having the following general formula (4):

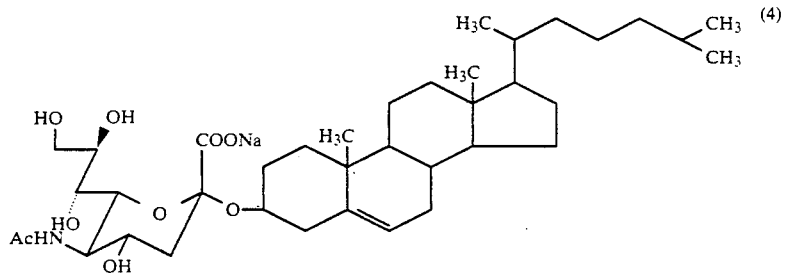

or the formula (5):

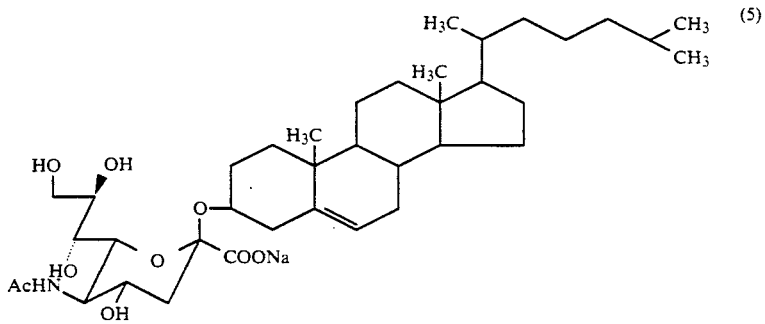

The present invention also relates to a process for producing the compound (4) or (5), which comprising reacting a compound (1) having a general formula (1):

with cholesterol, to produce a compound having a general formula (2):
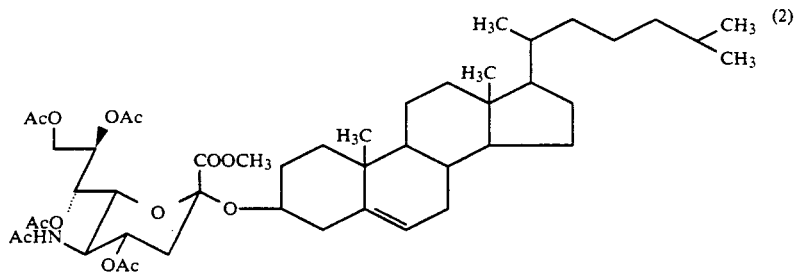
or the formula (3):
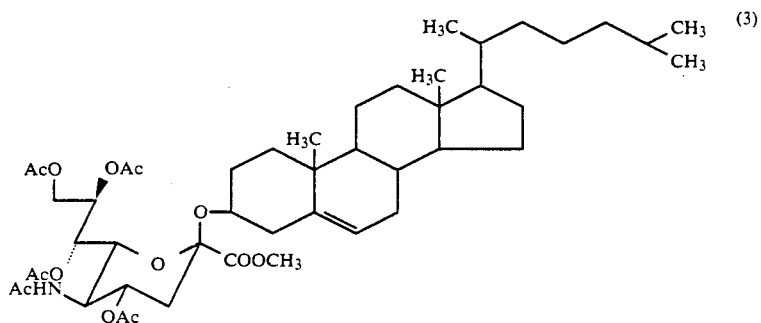
and then hydrolyzing the compound (2) or (3).
Further, the present invention relates to a neuropathy remedy containing the compound (4) or (5).
The present invention will be explained in detail below.
First, a process for producing the compound (4) or (5) will be summarized by the following scheme:

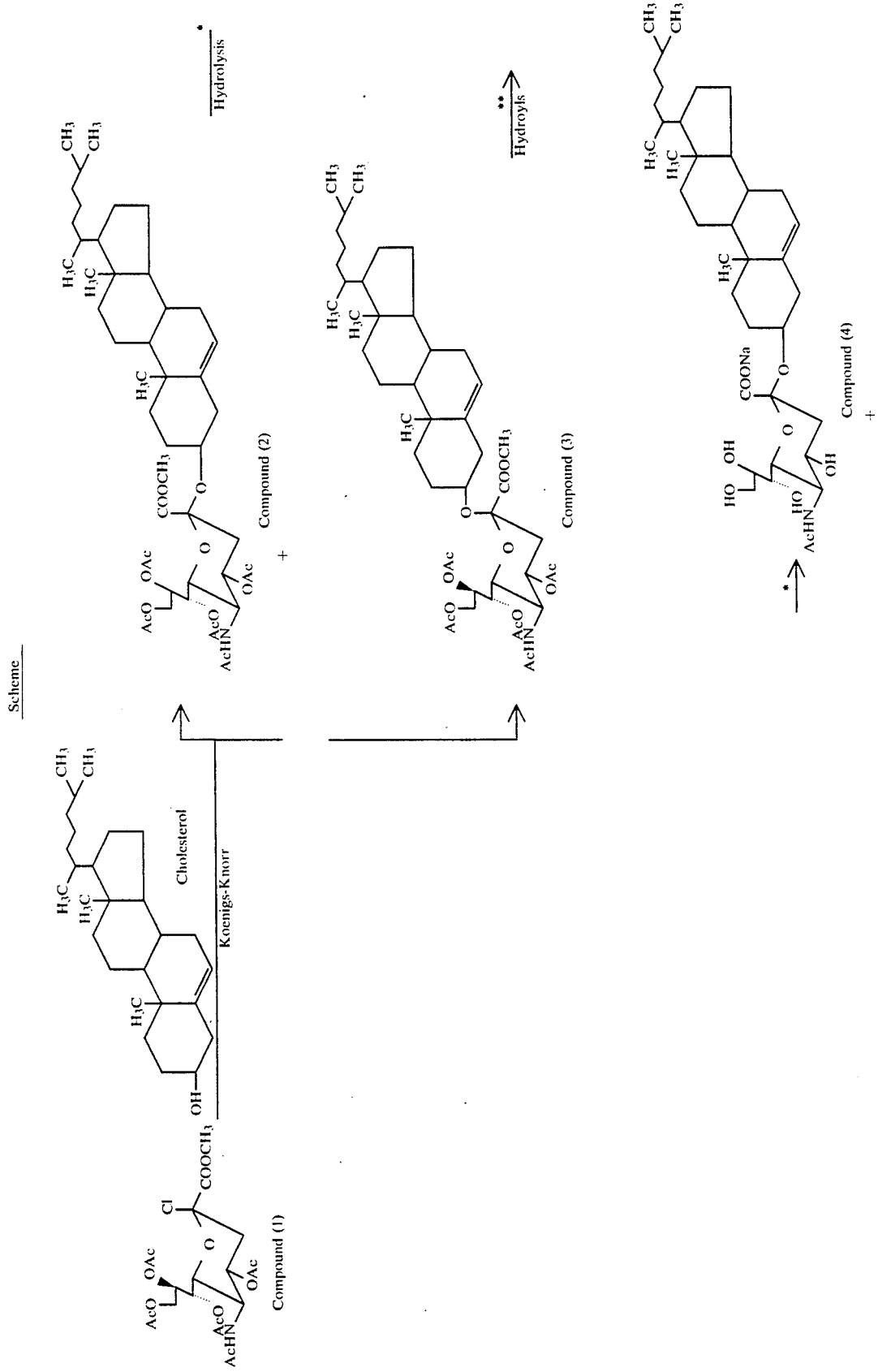

-continued
Scheme
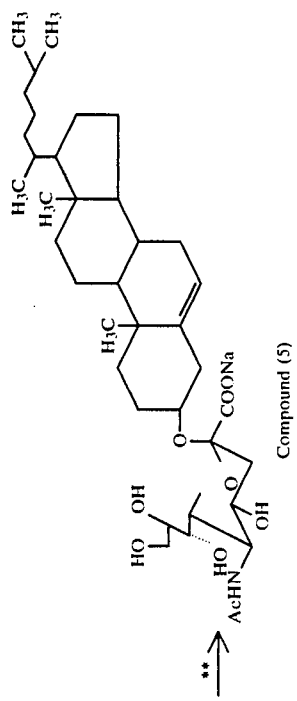
Compound (5)

The compound (1) to be used in the present invention is a known compound, and is commercially available.

In the above reaction, the compound (1) is reacted with cholesterol in the presence of a Koenigs-Knorr catalyst at about 20° to 25° C. under a normal pressure for about 1 to 7 days. In this case, cholesterol is reacted with the compound (1) at a molar ratio of about one to 5 moles of cholesterol to 1 mole of the compound (1).

The catalyst covers mercuric bromide, mercuric cyanide, silver perchlorate, silver trifluoromethanesulfonate, silver trifluoroacetate, and others. The catalyst is used in an amount of about 1.0 to 1.2 equivalent per one equivalent of the compound (1).

Solvents to be used in the present invention comprise acetonitrile, nitromethane, acetone, benzene, tetrahydrofuran, dichloromethane, and others. Among them, benzene, dichloromethane, and tetrahydrofuran are preferable solvents. In the present invention, a desiccant may be used. As a desiccant, Drierite or Molecular sieve 4A can be used.

The resultant compounds (2) and (3) are separated and purified by a conventional method such as a column chromatography.

The compounds are then hydrolyzed to convert their methoxy carbonyl groups into sodium carboxyl groups and convert their acetyl groups into hydrogen groups. By this hydrolysis, the compounds (4) and (5) can be produced. This hydrolysis is generally conducted by a conventional method. For example, the hydrolysis is conducted at about 15° to 25° C. for about 5 to 15 hours by treating the compounds with an alkaline solution at a concentration of about 1 to 3 N.

The present compound can be orally administered. However, it is preferable that the compound is administered by eye application, by inhalation, by intramuscular injection, by subcutaneous injection, or by intravenous injection. The administration amount varies depending on a degree of a disease and the weight of a patient. However, it is preferable that the amount is 0.001 to 10 mg.

EXAMPLE

The present invention will be explained in more detail by reference to the examples.

EXAMPLE 1

Synthesis of Methyl 5-Acetoamide-4,7,8,9-Tetra-O-Acetyl-2-O-Acetyl-2-O-(5-Cholesten-3-beta-yl)-3,5-Dideoxy-alpha -D-Glycero-D-Galacto-2-Nonulopyranosonate 0.77 g of cholesterol (2 m mol) which had been previously fully dried was dissolved in 10 ml of a solvent such as dried methylene chloride. After 0.5 g of Molecular sieve 4A which had been previously dried under vacuum at high temperature, was added to the cholesterol solution, the resultant mixture was stirred for 30 min. to one hour at room temperature in an argon stream. To this mixture, 1.02 g (2 m mol) of the compound (1) was added, and then 2 to 2.4 m mol of silver trifluoromethanesulfonate was added. Then, the resultant mixture was stirred for one night at room temperature under inclined light, to conduct the reaction.

The reaction solution was filtered by Celite. The silver salt was removed by saturated salt solution. The mixture was dried by anhydrous sodium sulfate, etc. Then, the solvent was distilled off by vacuum, to produce white solid.

The white solid was subjected to a column chromatography (silica gel), to separate the compounds (2) and (3) and purify them. 0.56 g (33%) of the compound (2) and 0.55 g (32%) of the compound (3) were obtained.

Physical properties of the compound (2):
Mass (EI) m/z 860 (M+1), 800 (M−59)
Elemental analysis (%) $C_{47}H_{73}O_{13}N$ Calculation C=65.63, H=8.55, N=1.63, Found C=65.41, H=8.61, N=1.60.
$[\alpha]_D^{25} -23.8°$ (C=1, chloroform)
m.p. 113°–115° C.
IR $\nu_{max}^{film}$ 3250, 2940, 1745, 1660 and 1540 cm$^{-1}$
$^1$H NMR CDCl$_3$ δ(TMS) 400 MHz 0.669 3H, s, CH$_3$-18 0.985 3H, s, CH$_3$-19 1.883 3H, s, NAc 2.026, 2.031, 2.126, 2.145, 3H×4, s×4, OAc×4 2.596 1H, dd, J=5.2, 12.8 Hz, 2' Heq 3.650 1H, m, H-3 3.790 3H, s, COOMe 4.02–4.09 2H, m, H-4', H-5' 4.166 1H, dd, J=5.8, 12.5 Hz, Ha-8' 4.347 1H, dd, J=2.5, 12.8 Hz, Hb-8' 4.854 1H, ddd, J=5.2, 9.8, 12.0 Hz, H-3' 5.205 1H, d, J=10.1 Hz, NH 5.33–5.37 2H, m, H-6', 7'

Physical properties of the compound (3):
Mass (EI) m/z 860 (M+1), 800 (M−59)
Elemental analysis (%) $C_{47}H_{73}O_{13}N$ Calculation C=65.63, H=8.55, N=1.63, Found C=65.89, H=8.58, N=1.66.
$[\alpha]_D^{25} -40.2°$ (C=1, chloroform)
m.p. 138°–140° C.
IR $\nu_{max}^{film}$ 3420, 3250, 2930, 1740, 1660 and 1540 cm$^{-1}$
$^1$H NMR CDCl$_3$ δ(TMS) 400 MHz 0.670 3H, s, CH$_3$-18 0.999 3H, s, CH$_3$-19 1.871 3H, s, NAc 2.021, 2.021, 2.077, 2.130, 3H×4, s×3, OAc×4 2.525 1H, dd, J=4.9, 13.1 Hz, Heq-2' 3.572 1H, m, H-3 3.798 3H, s, COOCH$_3$ 4.04–4.13 2H, m, H-4', 5' 4.146 1H, dd, J=7.6, 12.5 Hz, Ha-8' 4.888 1H, dd, J=1.8, 12.5 Hz, Hb-8' 5.07 1H, tt, J=2.0, 8.2 Hz, H-7' 5.22–5.27 1H, m, H-3' 5.34–5.38 2H, m, NH, H-6'

EXAMPLE 2

Synthesis of 5-Acetoamide-2-O-(5-Cholesten-3-beta-yl)-3,5-Dideoxy-alpha-D-Glycero-D-Galacto-2-Nonulopyranosonic acid The compound (2) obtained in Exapmle 1 was dissolved in 2 ml of methanol. 3 ml of a 1 N-sodium hydroxide aqueous solution was added to the solution, which was then stirred for one night at room temperature. After 2 ml of water was added to the resultant solution, the solution was neutralized by Dowex 50 (H+), a small amount of the precipitate was filtered off, and the filtrate was dried under vacuum, to produce 31.4 mg (79.7%) of the compound (4) (white powder).

30.0 mg (76.1%) of the compound (5) was obtained from the compound (3) in the same manner as the above.

Physical properties of the compound (4): IR $\nu_{max}^{KBr}$ 2750, 1570 cm$^{-1}$
$^1$H NMR CDCl$_3$ δ(TMS) 90 MHz 0.71 3H, s, CH$_3$-18 0.84 and 0.91 6H, CH$_3$-26 and CH$_3$-27 0.95 3H, d, J=4.5 Hz, CH$_3$-21 1.00 3H, s, CH$_3$-19 2.01 3H, s, NAc 2.43 1H, dd, J=4.5 and 12.6 Hz, 3-Heq
$[\alpha]_D^{22} -12.58°$ (C=0.41, in methanol)
Physical properties of the compound (5):
IR $\nu_{max}^{KBr}$ 2870, 1620 and 1550 cm$^{-1}$
$^1$H NMR CD$_3$OD δ(TMS) 90 MHz 0.71 3H, s, CH$_3$-18 0.86 and 0.92 6H, CH$_3$-26 and CH$_3$-27 0.95 3H, d, J=4.5 Hz, CH$_3$-21 1.00 3H, s, CH$_3$-19 2.00 3H, s, NAc 2.39 1H, dd, J=4.5 and 12.6 Hz, 3-Heq $[\alpha]_D^{20}$ −31.77° (C=0.78, in methanol)

EXAMPLE 3

50 mg of the compound (2), namely methyl 5-acetoamide-4,7,8,9-tetra-O-acetyl-2-O-(5-cholesten-3-beta-yl)-3,5-dideoxy-alpha-D-glycero-D-galacto-2-nonulopyranosonate, was dissolved in 100 ml of methanol. To this solution, about 20 ml of a 2 N-sodium hydroxide aqueous solution was dropped while stirring, to produce a sodium hydroxide/methanol solution of about 0.2 N, which was then stirred for one night at room temperature in order to saponify the compound.

Next, Dowex 50 W (H+) resin was added to the resultant solution while stirring. After the pH of the solution was adjusted acidic (about pH 4), the resin was removed. Then, the solution was dried under vacuum, to produce white powder 5-acetoamide-2-O-acetyl-(5-cholesten-3-beta-yl)-3,5-dideoxy-alpha-D-glycero-D-galacto-2-nonulopyranosonic acid. This powder was dissolved in a 0.02 N sodium hydroxide aqueous solution. The resultant solution was passed through a Dianon HP 20 resin column chromatography to cause adsorption on the resin, which resin was washed with water. Then, after elution was made with a 75% methanol aqueous solution, methanol was distilled off and freeze drying was made, to produce 37 mg (91%) of white powder sodium 5-acetoamide-2-O-(5-cholesten-3-yl)-3,5-dideoxy-alpha-D-glycero-D-galacto-2-nonulopyranosonate (the compound (4)). The physical properties of the compound (4) were substantially the same as those of Example 2.

EXAMPLE 4

50 mg of the compound (2) was dissolved in 100 ml of methanol, to which 20 ml of a 2 N sodium hydroxide aqueous solution was added. The resultant solution was stirred for one night at room temperature to cause saponification. After Dowex 50 W (H+) was added to the solution and the mixture was stirred, the pH of the mixture was controlled at 7 to 8. The mixture was subjected to suction filtration followed by methanol washing, so as to remove the resin. The filtrate and the washing methanol were collected and methanol was distilled off. The precipitated white undissolving material was filtered and then subjected to freeze drying, to produce 39 mg (96%) white powder (the compound (4)).

Physical properties of the compound (4):

Mass (FD) m/z 722 (M+Na), 700 (M+1), 386, 336 and 314

Elemental analysis (%) $C_{38}H_{62}O_9NNa \cdot 2H_2O$ Calculation C:61.96, H:8.42, N:1.90, Found C:61.92, H:8.71, N:2.04.

$[\alpha]_D^{24}$ +2.2° (C=1.0, methanol)

IR $\nu_{max}^{KBr}$ 3250, 2940 and 1605 cm$^{-1}$ $^1$H NMR CD$_3$OD $\delta$(TMS) 400 MHz 0.704 3H, s, CH$_3$-18 0.870 and 0.885 3H×2, d, J=1.7 Hz, CH$_3$-26, CH$_3$-27 0.936 3H, d, J=6.5 Hz, CH$_3$-21 0.992 3H, s, CH$_3$-19 2.010 3H, s, NAc 2.839 1H, dd, J=4.2 and 12.0 Hz, 2'-Heq 5.332 1H, d, J=5.5 Hz, 6-H $^{13}$C NMR CD$_3$OD $\delta$(TMS) 100 MHz 175.91 NAc, 175.26 1'-COONa 142.87 C-5 122.59 C-6 102.57 C-1' 70.50 C-3 41.00 C-2

EXAMPLE 5

Example 3 was repeated except that the compound (3), namely methyl 5-acetoamide-4,7,8,9-tetra-O-acetyl-2-O-(5-cholesten-3-beta-yl)-3,5-dideoxy-beta-D-glycero-D-galacto-2-nonulopyranosonate was used in place of the compound (2), to produce 36 mg (88%) of the compound (5), namely sodium 5-acetoamide-2-O-(5-cholesten-3-beta-yl)-3,5-dideoxy-beta-D-glycero-D-galacto-2-nonulopyranosonate. The physical properties of the compound (5) were substantially the same as those of Example 2.

EXAMPLE 6

Example 4 was repeated except that the compound (3) was used in place of the compound (2), to produce the compound (5) (40 mg, 98%).

Physical properties of the compound (5):

Mass (FD) m/z 722 (M+Na), 700 (M+1) and 386

Elemental analysis (%) $C_{38}H_{62}O_9NNa \cdot H_2O$ Calculation C:63.52, H:8.91, N:1.95, Found C:63.81, H:9.25, N:2.13.

$[\alpha]_D^{24}$ −10.6° (C=1.0, methanol)

IR $\nu_{max}^{KBr}$ 3270, 2950 and 1608 cm$^{-1}$ $^1$H NMR CD$_3$OD $\delta$(TMS) 400 MHz 0.700 3H, s, CH$_3$-18 0.861 and 0.880 3H×2, d, J=1.5 Hz, CH$_3$-26, CH$_3$-27 0.928 3H, d, J=6.5 Hz, CH$_3$-21 0.991 3H, s, CH$_3$-19 1.972 3H, s, NAc 2.482 1H, dd, J=4.5 and 13.0 Hz, 2'-Heq 5.282 1H, d, J=5.3 Hz, 6-H $^{13}$C NMR CD$_3$OD $\delta$(TMS) 100 MHz 176.95 NAc, 174.51 1'-COONa 143.08 C-5 122.46 C-6 101.37 C-1' 72.37 C-3 43.82 C-2'

EXAMPLE 7

50 mg of the compound (2) was dissolved in 100 ml of anhydrous methanol. To this solution, 0.02 ml of a 28% sodium methylate solution was added and then the resultant solution was stirred for about one hour at room temperature, to cause deacetylation. Then, Dowex 50 Wx8 (H+) resin was added to the resultant solution, which solution was stirred and neutralized. The solution was filtered by suction and methanol washing was made, to remove the resin. The filtrate and washing methanol were collected and then 20 ml of a 2 N sodium hydroxide aqueous solution was added to the solution, which was stirred for one night at room temperature to cause saponification. Amberlite IRC-50 (H+) resin was added to the saponified solution. The resultant solution was stirred and the pH thereof was controlled at 5 to 7. The solution was subjected to suction filtration followed by methanol washing, to remove the resin. The filtrate and washing methanol were collected and subjected to vacuum drying to distill off methanol. A small amount of the precipitated white undissolving material was filtered and subjected to freeze drying, to produce 38 mg (93%) of white powder (the compound (4)). The physical properties of the compound were substantially the same as those of Example 2.

EXAMPLE 8

Example 7 was repeated except that the compound (3) was used in place of the compound (2), to produce 35 mg (86%) of the compound (5). The physical properties of the compound were substantially the same as those of Example 2.

EXAMPLE 9

Injection composition

Into an ampule, there were introduced 2.5 mg of the present compound, 0.25 mg of sodium dihydrogen phosphate dihydrate, 3 mg of disodium hydrogen phosphate 12-water, and distilled water for injection, to produce an injection composition having a total amount of 1 ml.

EXAMPLE 10

Injection composition to be dissolved before use

An injection composition prepared by mixing 0.5 mg of the present compound with 1 ml of physiological saline and then subjecting it to freeze drying, was introduced into a vial and 1 ml of distilled water for injection was added to the vial, to dissolve the injection composition.

EXAMPLE 11

Composition for eye application

Into a vial, there were introduced 1 mg of the present compound, 52.5 mg of boric acid, 14.5 mg of borax, suitable amount of benzalkonium chloride, and a solubilizing solution for eye application, to produce an eye application composition having a total amount of 5 ml.

EXAMPLE 12

Inhalation composition

The present compound was well pulverized in an agate mortar into fine powder having a diameter of 1 to 20 micron. Lactose was added to the powder, and pulverized and mixed with each other. Further, lactose was added to the mixture little by little and they were finely pulverized and well mixed with each other, to prepare a 20 to 40 trituration. 20 to 40 mg of the powder was introduced into a capsule or folded by a powder paper by means of a conventional method. The capsule was used for powder aerosol. The folded powder was used for liquid aerosol.

Experiments for confirming the activity of the present compound for promoting propagation of neurites will be explained below.

Experiment 1

Effect on proliferation of neuroblastoma cell, Neuro 2a strain

Neuro 2a was floated on culture medium consisting of 90% of Dulbecco's Modified Eagle's Midium, and 10% of fetal calf serum (FCS), and containing 100 units/ml of penicillin G and 100 micro g/ml of streptomycin sulfate, and then cultivated at 37° C. in a carbon dioxide incubator containing air into which 5% of carbon dioxide was incorporated. The vessel as used was a polystyrene tray having a diameter of 60 mm. 1 to $2 \times 10^4$ of the neuroblastoma cells were implanted in each tray and cultivated for 48 hours. The FCS-containing culture was removed from the resultant cell culture. To the culture which did not contain the FCS (this culture contained 100% of MEM, and the concentrations of the antibiotics were the same as those of the culture before the remove of the FCS), there were added as test samples, the compound (4) (Table 1), the compound (5) (Table 2), Gal (beta 1-3) GalNac (beta 1-4) <NAcNeu-(alpha 2-3)>Gal (beta 1-4) Glc (beta 1-1)Ceramide (hereinafter referred to as GM) (Table 3), and <NAcNeu (alpha 2-8) NAcNeu (alpha 2-3)>Gal (beta 1-3) GalNAc (beta 1-4)- NAcNeu-(alpha 2-8) <NAcNeu- (alpha 2-3)>-Gal (beta 1-4) Glc (beta 1-1)-Ceramide (hereinafter referred to as $GQ_{1b}$) (Table 4), respectively in prescribed amounts, and the cultivation was continued. When 24 and 48 hours had passed after the addition of these medicines, the number of the living cells increased in the culture, the number of the neurites increased, and the length of the neurites were measured. The experiment was conducted on three trays with respect to each concentration. The resultant data were expressed by average value +standard error (S.E).

Results

The minimal effective concentrations of the compound (4), $GM_1$ and $GQ_{1b}$ in 48 hours after these medicines were added to the culture, were respectively 10 ng/ml, 10 micro g/ml, and 10 micro g/ml. Taking the molecular weights of these materials into consideration, the activity of the compound (4) is 420 times as high as that of $GM_1$ and 270 times as high as that of $GQ_{1b}$. The minimal effective concentration of the compound (5) is 100 ng/ml in 48 hours after the addition of the medicine, and the activity of the compound (5) is 42 times as high as that of $GM_1$ and 27 times as high as that of $GQ_{1b}$.

Further, $GM_1$ and $GQ_{1b}$ do not provide any activity when the cultivation was conducted for 24 hours. However, the compounds (4) and (5) indicated activity when the cultivation was conducted for 24 hours using these compounds in an amount of 10 ng/ml. These results clearly show that the compounds (4) and (5) have strong activity for the propagation of the neurites.

Acute Toxicity Test

Acute toxicity test was conducted by intravenously injecting the compounds into ddy male mice of 45 weeks age. The results show that $LD_{50}$'s of the compounds (4) and (5) are respectively 93 mg/kg and 291 mg/kg.

TABLE 1

| Test sample | | Total number of cells | Number of neurite propagated cells | Rate of neurite propagation (%) | Length of neurite ± S.E. (μm/cell) | Number of neurites ± S.E. (number/cell) |
|---|---|---|---|---|---|---|
| 24 hrs | | | | | | |
| CONTROL | | 417 | 169 | 40.5 | 79.4 ± 2.43 | 1.3 ± 0.04 |
| Compound (4) | 10 ng/ml | 416 | 131 | 31.5 | 92.4 ± 5.31*** | 1.2 ± 0.04 |
| Compound (4) | 100 ng/ml | 427 | 177 | 41.5 | 96.7 ± 4.12* | 1.2 ± 0.03 |
| Compound (4) | 1 μg/ml | 373 | 190 | 50.9 | 130.4 ± 6.12* | 1.2 ± 0.03 |
| Compound (4) | 10 μg/ml | U.C. | U.C. | — | U.C. | U.C. |
| 48 hrs | | | | | | |
| CONTROL | | 483 | 206 | 42.7 | 103.6 ± 4.08 | 1.2 ± 0.03 |
| Compound (4) | 10 ng/ml | 467 | 219 | 46.9 | 121.9 ± 5.18** | 1.2 ± 0.03 |
| Compound (4) | 100 ng/ml | 404 | 193 | 47.8 | 126.0 ± 6.10** | 1.2 ± 0.04 |
| Compound (4) | 1 μg/ml | 369 | 182 | 49.3 | 156.3 ± 8.32* | 1.2 ± 0.04 |
| Compound (4) | 10 μg/ml | U.C. | U.C. | — | U.C. | U.C. |

U.C.: unmeasurable
*$p < 0.001$, $p < 0.01$, *$p < 0.05$

TABLE 2

| Test sample | | Total number of cells | Number of neurite propagated cells | Rate of neurite propagation (%) | Length of neurite ± S.E. (μm/cell) | Number of neurites ± S.E. (number/cell) |
|---|---|---|---|---|---|---|
| 24 hrs | | | | | | |
| CONTROL | | 417 | 169 | 40.5 | 79.4 ± 2.43 | 1.3 ± 0.04 |
| Compound (5) | 10 ng/ml | 361 | 124 | 34.3 | 89.4 ± 4.23*** | 1.3 ± 0.05 |
| Compound (5) | 100 ng/ml | 384 | 156 | 40.6 | 116.4 ± 5.59* | 1.2 ± 0.03 |
| Compound (5) | 1 μg/ml | 396 | 213 | 53.8 | 130.8 ± 5.16* | 1.2 ± 0.04 |
| Compound (5) | 10 μg/ml | U.C. | U.C. | — | U.C. | U.C. |
| 48 hrs | | | | | | |
| CONTROL | | 483 | 206 | 42.7 | 103.6 ± 4.08 | 1.2 ± 0.03 |
| Compound (5) | 10 ng/ml | 472 | 226 | 47.9 | 110.6 ± 4.93 | 1.2 ± 0.04 |
| Compound (5) | 100 ng/ml | 422 | 212 | 50.2 | 135.1 ± 6.23* | 1.3 ± 0.04 |
| Compound (5) | 1 μg/ml | 454 | 252 | 55.5 | 138.9 ± 5.39* | 1.2 ± 0.03 |
| Compound (5) | 10 μg/ml | U.C. | U.C. | — | U.C. | U.C. |

U.C.: unmeasurable
*p < 0.001. p < 0.01. *p < 0.05

TABLE 3

| Test sample | | Total number of cells | Number of neurite propagated cells | Rate of neurite propagation (%) | Length of neurite ± S.E. (μm/cell) | Number of neurites ± S.E. (number/cell) |
|---|---|---|---|---|---|---|
| 24 hrs | | | | | | |
| CONTROL | | 320 | 146 | 45.6 | 101.0 ± 6.04 | 1.3 ± 0.05 |
| $GM_1$ | 10 ng/ml | 334 | 145 | 43.4 | 94.9 ± 6.64 | 1.4 ± 0.05 |
| $GM_1$ | 100 ng/ml | 297 | 142 | 47.8 | 101.1 ± 5.09 | 1.4 ± 0.06 |
| $GM_1$ | 1 μg/ml | 332 | 140 | 42.2 | 109.7 ± 6.44 | 1.4 ± 0.06 |
| $GM_1$ | 10 μg/ml | 325 | 149 | 45.8 | 89.3 ± 4.77 | 1.4 ± 0.05 |
| $GM_1$ | 100 μg/ml | 310 | 172 | 55.5 | 90.5 ± 3.88 | 1.8 ± 0.06 |
| 48 hrs | | | | | | |
| CONTROL | | 383 | 184 | 48.0 | 95.8 ± 4.61 | 1.4 ± 0.05 |
| $GM_1$ | 10 ng/ml | 333 | 194 | 58.3 | 93.7 ± 5.07 | 1.4 ± 0.05 |
| $GM_1$ | 100 ng/ml | 349 | 156 | 44.7 | 108.8 ± 5.97 | 1.4 ± 0.06 |
| $GM_1$ | 1 μg/ml | 352 | 211 | 59.9 | 109.2 ± 6.09 | 1.3 ± 0.04 |
| $GM_1$ | 10 μg/ml | 330 | 205 | 62.1 | 113.8 ± 5.49*** | 1.3 ± 0.04 |
| $GM_1$ | 100 μg/ml | 317 | 193 | 60.9 | 98.9 ± 5.22 | 1.5 ± 0.05 |

***p < 0.05

TABLE 4

| Test sample | | Total number of cells | Number of neurite propagated cells | Rate of neurite propagation (%) | Length of neurite ± S.E. (μm/cell) | Number of neurites ± S.E. (number/cell) |
|---|---|---|---|---|---|---|
| 24 hrs | | | | | | |
| CONTROL | | 320 | 146 | 45.6 | 101.0 ± 6.04 | 1.3 ± 0.05 |
| $CQ_{1b}$ | 10 ng/ml | 336 | 174 | 51.8 | 88.5 ± 5.00 | 1.3 ± 0.05 |
| $CQ_{1b}$ | 100 ng/ml | 331 | 159 | 48.0 | 86.0 ± 4.72 | 1.3 ± 0.04 |
| $CQ_{1b}$ | 1 μg/ml | 308 | 157 | 51.0 | 97.6 ± 4.95 | 1.4 ± 0.05 |
| $CQ_{1b}$ | 10 μg/ml | 321 | 205 | 63.9 | 114.9 ± 5.98 | 1.4 ± 0.06 |
| $CQ_{1b}$ | 100 μg/ml | U.C. | U.C. | — | U.C. | U.C. |
| 48 hrs | | | | | | |
| CONTROL | | 383 | 184 | 48.0 | 95.8 ± 4.61 | 1.4 ± 0.05 |
| $CQ_{1b}$ | 10 ng/ml | 371 | 158 | 42.6 | 100.4 ± 5.76 | 1.5 ± 0.06 |
| $CQ_{1b}$ | 100 ng/ml | 347 | 153 | 44.1 | 90.4 ± 6.06 | 1.2 ± 0.04 |
| $CQ_{1b}$ | 1 μg/ml | 384 | 182 | 47.4 | 106.5 ± 6.40 | 1.3 ± 0.04 |
| $CQ_{1b}$ | 10 μg/ml | 346 | 214 | 61.8 | 122.5 ± 6.99** | 1.3 ± 0.04 |
| $CQ_{1b}$ | 100 μg/ml | U.C. | U.C. | — | U.C. | U.C |

U.C.: unmeasurable
***p < 0.01

The present sialosyl cholesterol is useful, in particular, for a neuropathy remedy.

What is claimed is:

1. Sialosyl cholesterol having the following formula (4) or (5):

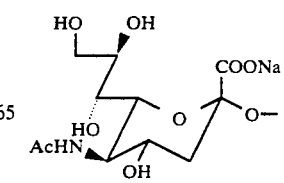

(4)

-continued
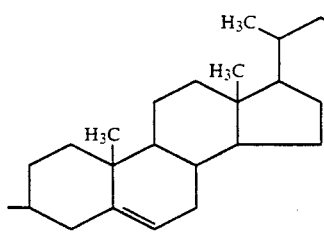
or
-continued
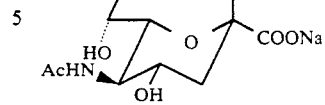
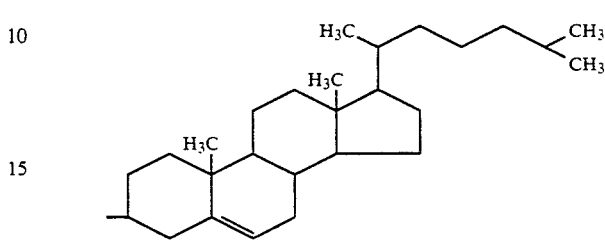
wherein Ac is an acetyl group.
2. A method for treating neuropathy, comprising administering an antineuropathy effective amount of the sialosyl cholesterol of claim 1 to a patient in need thereof.
* * * * *